(12) United States Patent
Ishii et al.

(10) Patent No.: US 8,460,311 B2
(45) Date of Patent: Jun. 11, 2013

(54) INTRAOCULAR LENS IMPLANTING DEVICE

(75) Inventors: Kiyoshi Ishii, Tokyo (JP); Katsutoshi Kubota, Kodama-machi (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 11/722,601

(22) PCT Filed: Dec. 19, 2005

(86) PCT No.: PCT/JP2005/023246
§ 371 (c)(1),
(2), (4) Date: Jun. 22, 2007

(87) PCT Pub. No.: WO2006/070628
PCT Pub. Date: Jul. 6, 2006

(65) Prior Publication Data
US 2008/0086146 A1   Apr. 10, 2008

(30) Foreign Application Priority Data
Dec. 27, 2004   (JP) .................. 2004-377175

(51) Int. Cl.
*A61F 9/00* (2006.01)
(52) U.S. Cl.
USPC .......................... 606/107; 623/6.12
(58) Field of Classification Search
USPC .......................... 606/107; 623/6.12
See application file for complete search history.

(56) References Cited

U.S. PATENT DOCUMENTS

| | | | |
|---|---|---|---|
| 2,761,446 | A | 9/1956 | Reed |
| 4,205,747 | A | 6/1980 | Gilliam et al. |
| 4,269,307 | A | 5/1981 | LaHaye |
| 4,423,809 | A | 1/1984 | Mazzocco |
| 4,573,998 | A | 3/1986 | Mazzocco |
| 4,608,049 | A | 8/1986 | Kelman |
| 4,634,423 | A | 1/1987 | Bailey |
| 4,681,102 | A | 7/1987 | Bartell |
| 4,697,697 | A | 10/1987 | Graham et al. |
| 4,699,140 | A | 10/1987 | Holmes |
| 4,702,244 | A | 10/1987 | Mazzocco |
| 4,747,404 | A | 5/1988 | Jampel et al. |
| 4,750,498 | A | 6/1988 | Graham |
| 4,759,359 | A | 7/1988 | Willis et al. |
| 4,763,650 | A | 8/1988 | Hauser |
| 4,765,329 | A | 8/1988 | Cumming et al. |

(Continued)

FOREIGN PATENT DOCUMENTS

| | | |
|---|---|---|
| DE | 3610925 | 10/1987 |
| DE | 4110278 | 10/1992 |

(Continued)

*Primary Examiner* — S. Thomas Hughes
*Assistant Examiner* — Julie A Szpira
(74) *Attorney, Agent, or Firm* — Henricks, Slavin & Holmes LLP (57) ABSTRACT

An intraocular lens implanting device capable of inserting an intraocular lens surely in safety into an eyeball and having an ophthalmic hooking function capable of adjusting the position of the intraocular lens. The intraocular lens implanting device for inserting an intraocular lens into an eyeball through an incision in the eyeball tissue comprises a tubular main body, a storage part for the intraocular lens integrated with the main body or separated therefrom, and a plunger for pressing the intraocular lens placed in the containing section and discharging it into the eyeball, wherein the distal end of the plunger has a base part and a protuberance.

13 Claims, 9 Drawing Sheets

U.S. PATENT DOCUMENTS

| | | | |
|---|---|---|---|
| 4,769,034 A | 9/1988 | Poley | |
| 4,781,719 A | 11/1988 | Kelman | |
| 4,787,904 A | 11/1988 | Severin | |
| 4,819,631 A | 4/1989 | Poley | |
| 4,834,094 A | 5/1989 | Patton | |
| 4,836,201 A | 6/1989 | Patton | |
| 4,862,885 A | 9/1989 | Cumming | |
| 4,880,000 A | 11/1989 | Holmes et al. | |
| 4,919,130 A | 4/1990 | Stoy et al. | |
| 4,934,363 A | 6/1990 | Smith et al. | |
| 4,955,889 A | 9/1990 | Van Gent | |
| 4,976,716 A | 12/1990 | Cumming | |
| 4,988,352 A | 1/1991 | Poley | |
| 4,994,028 A | 2/1991 | Leonard et al. | |
| 5,066,297 A | 11/1991 | Cumming | |
| 5,098,439 A | 3/1992 | Hill et al. | |
| 5,123,905 A | 6/1992 | Kelman | |
| 5,139,501 A | 8/1992 | Klaas | |
| 5,171,241 A | 12/1992 | Buboltz et al. | |
| 5,176,686 A | 1/1993 | Poley | |
| 5,178,622 A | 1/1993 | Lehner | |
| 5,190,552 A | 3/1993 | Kelman | |
| 5,190,553 A | 3/1993 | Kanert et al. | |
| 5,222,972 A | 6/1993 | Hill et al. | |
| 5,242,450 A | 9/1993 | McDonald | |
| 5,275,604 A | 1/1994 | Rheinish et al. | |
| 5,281,227 A | 1/1994 | Sussman | |
| 5,304,182 A | 4/1994 | Rheinish et al. | |
| 5,354,333 A | 10/1994 | Kammann et al. | |
| 5,395,378 A | 3/1995 | McDonald | |
| 5,425,734 A | 6/1995 | Blake | |
| 5,454,818 A | 10/1995 | Hambleton et al. | |
| 5,468,246 A | 11/1995 | Blake | |
| 5,474,562 A | 12/1995 | Orchowski et al. | |
| 5,494,484 A | 2/1996 | Feingold | |
| 5,496,328 A | 3/1996 | Nakajima et al. | |
| 5,499,987 A | 3/1996 | Feingold | |
| 5,562,676 A | 10/1996 | Brady et al. | |
| 5,571,113 A | 11/1996 | McDonald | |
| 5,578,042 A | 11/1996 | Cumming | |
| 5,582,613 A | 12/1996 | Brady | |
| 5,582,614 A | 12/1996 | Feingold | |
| 5,584,304 A | 12/1996 | Brady | |
| 5,616,148 A | 4/1997 | Eagles et al. | |
| 5,620,450 A | 4/1997 | Eagles et al. | |
| 5,643,275 A | 7/1997 | Blake | |
| 5,643,276 A | 7/1997 | Zaleski | |
| 5,653,715 A | 8/1997 | Reich et al. | |
| 5,653,753 A | 8/1997 | Brady et al. | |
| 5,702,402 A | 12/1997 | Brady | |
| 5,702,441 A | 12/1997 | Zhou | |
| 5,716,364 A | 2/1998 | Makker et al. | |
| 5,728,102 A | 3/1998 | Feingold et al. | |
| 5,735,858 A | 4/1998 | Makker et al. | |
| 5,766,181 A | 6/1998 | Chambers et al. | |
| 5,772,666 A | 6/1998 | Feingold et al. | |
| 5,772,667 A | 6/1998 | Blake | |
| 5,776,138 A | 7/1998 | Vidal et al. | |
| 5,800,442 A | 9/1998 | Wolf et al. | |
| 5,803,925 A | 9/1998 | Yang et al. | |
| 5,807,400 A | 9/1998 | Chambers et al. | |
| 5,810,833 A | 9/1998 | Brady et al. | |
| 5,810,834 A | 9/1998 | Heyman | |
| 5,860,984 A | 1/1999 | Chambers et al. | |
| 5,860,986 A | 1/1999 | Reich et al. | |
| 5,868,751 A | 2/1999 | Feingold | |
| 5,868,752 A | 2/1999 | Makker et al. | |
| 5,873,879 A | 2/1999 | Figueroa et al. | |
| 5,876,406 A | 3/1999 | Wolf et al. | |
| 5,876,407 A | 3/1999 | Makker et al. | |
| 5,876,440 A | 3/1999 | Feingold | |
| 5,891,152 A | 4/1999 | Feingold | |
| 5,902,307 A | 5/1999 | Feingold et al. | |
| 5,919,197 A | 7/1999 | McDonald | |
| 5,921,989 A | 7/1999 | Deacon et al. | |
| 5,928,245 A | 7/1999 | Wolf et al. | |
| 5,941,886 A | 8/1999 | Feingold | |
| 5,942,277 A | 8/1999 | Makker et al. | |
| 5,944,725 A | 8/1999 | Cicenas | |
| 5,947,974 A | 9/1999 | Brady et al. | |
| 5,947,975 A | 9/1999 | Kikuchi et al. | |
| 5,957,748 A | 9/1999 | Ichiha | |
| 6,001,107 A | 12/1999 | Feingold | |
| 6,010,510 A | 1/2000 | Brown et al. | |
| 6,022,358 A | 2/2000 | Wolf et al. | |
| 6,048,348 A | 4/2000 | Chambers et al. | |
| 6,051,000 A | 4/2000 | Heyman | |
| 6,056,757 A | 5/2000 | Feingold et al. | |
| 6,056,758 A | 5/2000 | Vidal et al. | |
| 6,059,791 A | 5/2000 | Chambers | |
| 6,074,397 A | 6/2000 | Chambers et al. | |
| 6,083,230 A | 7/2000 | Makker et al. | |
| 6,093,193 A | 7/2000 | Makker et al. | |
| 6,129,733 A | 10/2000 | Brady et al. | |
| 6,142,999 A | 11/2000 | Brady et al. | |
| 6,143,000 A | 11/2000 | Feingold | |
| 6,162,229 A * | 12/2000 | Feingold et al. | 606/107 |
| 6,174,315 B1 | 1/2001 | Chambers et al. | |
| 6,214,015 B1 | 4/2001 | Reich et al. | |
| 6,241,737 B1 | 6/2001 | Feingold | |
| 6,248,111 B1 | 6/2001 | Glick et al. | |
| 6,251,114 B1 | 6/2001 | Farmer et al. | |
| 6,254,607 B1 | 7/2001 | Makker et al. | |
| 6,267,768 B1 | 7/2001 | Deacon | |
| 6,283,975 B1 | 9/2001 | Glick et al. | |
| 6,283,976 B1 | 9/2001 | Portney | |
| 6,312,433 B1 | 11/2001 | Butts | |
| 6,334,862 B1 | 1/2002 | Vidal et al. | |
| 6,336,932 B1 | 1/2002 | Figueroa et al. | |
| 6,355,046 B2 | 3/2002 | Kikuchi et al. | |
| 6,371,960 B2 | 4/2002 | Heyman et al. | |
| 6,386,357 B1 | 5/2002 | Egawa | |
| 6,387,101 B1 | 5/2002 | Butts et al. | |
| 6,398,788 B1 | 6/2002 | Makker et al. | |
| 6,406,481 B2 | 6/2002 | Feingold et al. | |
| 6,428,545 B2 | 8/2002 | Portney | |
| 6,447,519 B1 | 9/2002 | Brady et al. | |
| 6,447,520 B1 * | 9/2002 | Ott et al. | 606/107 |
| 6,468,282 B2 | 10/2002 | Kikuchi et al. | |
| 6,471,708 B2 | 10/2002 | Green | |
| 6,491,697 B1 | 12/2002 | Clark et al. | |
| 6,500,181 B1 | 12/2002 | Portney | |
| 6,506,195 B2 | 1/2003 | Chambers et al. | |
| 6,537,283 B2 | 3/2003 | Van Noy | |
| 6,540,754 B2 | 4/2003 | Brady | |
| 6,554,839 B2 * | 4/2003 | Brady | 606/107 |
| 6,558,395 B2 | 5/2003 | Hjertman et al. | |
| 6,607,537 B1 | 8/2003 | Binder | |
| 6,629,979 B1 | 10/2003 | Feingold | |
| 6,666,871 B2 | 12/2003 | Kikuchi et al. | |
| 6,679,891 B2 | 1/2004 | Makker et al. | |
| 6,685,740 B2 | 2/2004 | Figueroa et al. | |
| 6,712,848 B1 | 3/2004 | Wolf et al. | |
| 6,723,104 B2 * | 4/2004 | Ott | 606/107 |
| 6,733,507 B2 | 5/2004 | McNicholas et al. | |
| 6,858,033 B2 | 2/2005 | Kobayashi | |
| 6,921,405 B2 | 7/2005 | Feingold et al. | |
| 6,923,815 B2 * | 8/2005 | Brady et al. | 606/107 |
| 7,014,641 B2 | 3/2006 | Kobayashi et al. | |
| 7,025,782 B2 | 4/2006 | Kobayashi et al. | |
| 7,033,366 B2 | 4/2006 | Brady | |
| 7,037,312 B2 | 5/2006 | Kikuchi et al. | |
| 7,074,227 B2 | 7/2006 | Portney | |
| 7,097,649 B2 | 8/2006 | Meyer | |
| 7,131,976 B2 | 11/2006 | Kobayashi et al. | |
| 7,156,854 B2 | 1/2007 | Brown et al. | |
| 7,348,038 B2 | 3/2008 | Makker et al. | |
| 7,422,604 B2 | 9/2008 | Vaquero et al. | |
| 7,429,263 B2 | 9/2008 | Vaquero et al. | |
| 7,458,976 B2 | 12/2008 | Peterson et al. | |
| 7,476,230 B2 | 1/2009 | Ohno et al. | |
| 7,494,505 B2 | 2/2009 | Kappelhof et al. | |
| 7,645,300 B2 | 1/2010 | Tsai | |
| 2001/0007942 A1 | 7/2001 | Kikuchi et al. | |
| 2002/0103490 A1 | 8/2002 | Brady | |
| 2002/0151904 A1 * | 10/2002 | Feingold et al. | 606/107 |
| 2002/0165610 A1 * | 11/2002 | Waldock | 623/6.12 |

| | | | | | |
|---|---|---|---|---|---|
| 2002/0193805 A1 | 12/2002 | Ott et al. | JP | 11-113939 A | 4/1999 |
| 2003/0040755 A1 | 2/2003 | Meyer | JP | 11-506357 A | 6/1999 |
| 2003/0050647 A1* | 3/2003 | Brady .............. 606/107 | JP | 2000-516487 A | 12/2000 |
| 2003/0139749 A1 | 7/2003 | Kikuchi et al. | JP | 2000-516488 A | 12/2000 |
| 2003/0181921 A1 | 9/2003 | Jeannin | JP | 2001-502563 | 2/2001 |
| 2003/0195522 A1* | 10/2003 | McNicholas et al. ....... 606/107 | JP | 2001-104347 A | 4/2001 |
| 2003/0212406 A1 | 11/2003 | Kobayashi et al. | JP | 2002-516709 A | 6/2002 |
| 2003/0212407 A1 | 11/2003 | Kikuchi | JP | 2002-355268 A | 12/2002 |
| 2003/0212409 A1 | 11/2003 | Kobayashi et al. | JP | 2002-541912 A | 12/2002 |
| 2004/0111094 A1 | 6/2004 | Meyer | JP | 2003-144480 A | 5/2003 |
| 2004/0117012 A1 | 6/2004 | Vincent | JP | 3412106 B2 | 6/2003 |
| 2004/0238392 A1 | 12/2004 | Peterson et al. | JP | 2003-210498 A | 7/2003 |
| 2004/0243141 A1 | 12/2004 | Brown et al. | JP | 2003-325569 A | 11/2003 |
| 2005/0049606 A1 | 3/2005 | Vaquero et al. | JP | 2003-325570 A | 11/2003 |
| 2005/0125000 A1 | 6/2005 | Tourrette et al. | JP | 2003-325572 A | 11/2003 |
| 2005/0182419 A1 | 8/2005 | Tsai | JP | 2004-024854 A | 1/2004 |
| 2005/0222578 A1 | 10/2005 | Vaquero | JP | 2004-188194 A | 7/2004 |
| 2005/0261703 A1* | 11/2005 | Feingold et al. .............. 606/107 | JP | 2004-351196 A | 12/2004 |
| 2006/0085013 A1* | 4/2006 | Dusek et al. .................. 606/107 | JP | 2006-181269 A | 7/2006 |
| 2006/0167466 A1 | 7/2006 | Dusek | JP | 2006-297146 A | 11/2006 |
| 2006/0293694 A1 | 12/2006 | Futamura | JP | 2006-333924 A | 12/2006 |
| 2008/0033449 A1 | 2/2008 | Cole et al. | JP | 2006-333981 A | 12/2006 |
| 2008/0058830 A1 | 3/2008 | Cole et al. | JP | 2007-503872 A | 3/2007 |
| 2008/0221584 A1 | 9/2008 | Downer | JP | 2007-152010 A | 6/2007 |
| 2009/0036898 A1 | 2/2009 | Ichinohe | JP | 2007-181604 A | 7/2007 |
| 2009/0043313 A1 | 2/2009 | Ichinohe | JP | 2007-526091 A | 9/2007 |
| 2009/0112223 A1 | 4/2009 | Downer et al. | JP | 2008-521535 A | 6/2008 |
| 2009/0204122 A1 | 8/2009 | Ichinohe et al. | JP | 2008-212689 A | 9/2008 |
| 2009/0216244 A1 | 8/2009 | Pynson | WO | 94/07436 A1 | 4/1994 |
| 2009/0248031 A1 | 10/2009 | Ichinohe | WO | WO9513022 A1 | 5/1995 |
| 2010/0161049 A1 | 6/2010 | Inoue | WO | WO9628122 A1 | 9/1996 |
| 2010/0185206 A1 | 7/2010 | Ichinohe et al. | WO | 97/15253 A1 | 5/1997 |
| 2010/0217273 A1 | 8/2010 | Someya et al. | WO | WO9812969 A1 | 4/1998 |
| 2010/0286704 A1 | 11/2010 | Ichinohe et al. | WO | WO0045746 A1 | 8/2000 |
| 2011/0082463 A1 | 4/2011 | Inoue | WO | WO0062712 A1 | 10/2000 |
| 2011/0098717 A1 | 4/2011 | Inoue | WO | 02/071982 A1 | 9/2002 |
| 2011/0264101 A1 | 10/2011 | Inoue et al. | WO | WO02096322 A1 | 12/2002 |
| 2011/0270264 A1 | 11/2011 | Shoji et al. | WO | WO2005023154 A1 | 3/2005 |
| 2011/0288557 A1 | 11/2011 | Kudo et al. | WO | WO2005070341 A1 | 8/2005 |
| 2012/0022549 A1 | 1/2012 | Someya et al. | WO | WO2005084588 A1 | 9/2005 |
| 2012/0071887 A1 | 3/2012 | Ichinohe et al. | WO | WO2006070628 A1 | 7/2006 |

FOREIGN PATENT DOCUMENTS

| | | | | | |
|---|---|---|---|---|---|
| EP | 0363213 | 4/1990 | WO | WO2006080191 A1 | 8/2006 |
| EP | 0727966 | 9/2003 | WO | WO2006090531 A1 | 8/2006 |
| EP | 1832247 A1 | 9/2007 | WO | WO2007037223 A1 | 4/2007 |
| EP | 1338254 | 12/2008 | WO | WO2007097221 A1 | 4/2007 |
| FR | 2749752 A | 12/1997 | WO | WO2007080869 A1 | 7/2007 |
| JP | 63-197453 A | 8/1988 | WO | WO2008149794 A1 | 12/2008 |
| JP | 4-212350 A | 8/1992 | WO | WO2008149795 A1 | 12/2008 |
| JP | 5-103808 | 4/1993 | WO | WO2009058929 A1 | 7/2009 |
| JP | 5-103809 | 4/1993 | WO | WO2009148091 A1 | 12/2009 |
| JP | 8-024282 A | 1/1996 | WO | WO2011126144 A1 | 10/2011 |
| JP | 8-505540 A | 6/1996 | WO | WO2011155636 A1 | 12/2011 |
| JP | 9-506285 A | 6/1997 | | | |

* cited by examiner

INTRAOCULAR LENS IMPLANTING DEVICE

CROSS REFERENCE TO RELATED APPLICATIONS

This is a U.S. national phase application under 35 U.S.C. §371 of International Patent Application No. PCT/JP2005/023246, filed Dec. 19, 2005 and claims the benefit of Japanese application 2004-377175 filed Dec. 27, 2004. The International Application was published in Japanese on Jul. 6, 2006 as International Publication No. WO 2006/070628 under PCT Article 21(2), the content of which are incorporated herein in its entirety.

TECHNICAL FIELD

The present invention relates to an implanting device for implanting an intraocular lens into an eyeball in place of a crystalline lens which has been extracted by cataract surgery; and specifically relates to an intraocular lens implanting device wherein a foldable intraocular lens is stored in a storage part, pressed in with a plunger, passed through an incision in the eyeball tissue, and implanted therein.

BACKGROUND ART

Artificial crystalline lenses are often implanted in the eye to replace a crystalline lens which has been extracted via cataract surgery. In a modern cataract surgery and the accompanying implantation of an artificial crystalline lens, the most important matter of concern is that the surgery be minimally invasive. Making the incision in the eyeball tissue smaller is expected to have the effect of alleviating postoperative astigmatism, and making the incision smaller as well as reducing the surgery time are expected to reduce the occurrence of postoperative inflammation. Specifically, making a smaller incision in the eyeball tissue and reducing the time of a series of surgeries has the merits of promoting faster post-op eyesight recovery and alleviating the burdens imposed by surgery on both the patient and the surgeon.

Phacoemulsification is often used in modern cataract surgery, and it is possible to leave the crystalline lens capsule while extracting an opacified crystalline lens nucleus through an incision of about 2.8 mm in the eyeball tissue.

An artificial intraocular lens implanted in place of the extracted crystalline lens is implanted in the remaining crystalline lens capsule. Following the invention of foldable intraocular lenses, it has even been possible to insert an intraocular lens having an optical diameter of 6 mm into an incision of about 4 mm in the eyeball tissue by folding the lens in half. Furthermore, to insert an artificial intraocular lens into the eye through a small incision, a method has recently been proposed wherein the intraocular lens is folded and stored in a storage cartridge, and is pressed in and implanted with a plunger. It is possible to implant an artificial intraocular lens into the eye without widening the incision made in the eyeball tissue for phacoemulsification purposes.

One example of a specific method for implanting the artificial intraocular lens into the eyeball by using a cartridge and a plunger is an intraocular lens insertion system (see Japanese Publication No. 8-505540, for example) configured from a plunger, a cartridge, and a hand piece as a cylindrical main body. This intraocular lens insertion system has a lens compartment in the cartridge, and the intraocular lens placed in the lens compartment can be folded over by closing the lens compartment. After the lens is folded, the cartridge is mounted on the hand piece and the plunger is pressed in, whereby the intraocular lens can be implanted into the eye.

Since the distal end of the plunger has a unique bifurcated shape, the supporting part of the intraocular lens can be prevented from being crushed between and damaged by the inner wall of the cartridge and the distal end of the plunger when the intraocular lens is passed through the cartridge interior. Also, after the intraocular lens is inserted into the eye, the distal end of the bifurcated plunger can be used to adjust the position of the intraocular lens to a specific position.

SUMMARY OF THE INVENTION

However, the conventional technique described above has the following problems. One problem arises from the distal end of the plunger being bifurcated and the middle being hollowed. Specifically, since the plunger has a complicated shape having two protuberances for holding down the periphery of the intraocular lens, the pressure applied to the intraocular lens from the plunger when the intraocular lens is pushed out may concentrate in a particular region of the distal end of the plunger, and may damage the optical surface of the intraocular lens. Another problem is that since the structure is complicated, production costs are high.

Another problem arises from the folding mechanism being attached to the cartridge itself. In the method for implanting an intraocular lens into the eyeball by using an insertion cylinder and a plunger, a cartridge is used wherein the insertion cylinder, the lens compartment, and the lens-folding part are formed integrally. The structure of the folding part therefore has restrictions, and it has been difficult to fold the intraocular lens into the desired shape. As a result, the operator must be skilled and experienced.

Specifically, the intraocular lens is composed of an optical part having a substantially circular shape in plan view, and multiple barb-shaped supporting parts for holding the lens at a specific position in the eye. The positional relationships between the optical part and the supporting parts is extremely important in the processes for folding the intraocular lens, inserting the lens into the eye, and setting the lens in place in the eye. If these positional relationships are inadequate or occasionally unstable, this causes problems in that a long time is spent setting the intraocular lens in place at a specific position, and a large burden is imposed on the operator and the patient. Various shapes are possible for the supporting parts of the intraocular lens, such as plate shapes instead of barb shapes, but the same problems are encountered with an intraocular lens having plate-shaped supporting parts.

The present invention was designed in order to resolve the problems encountered with the conventional technique described above, and an object thereof is to provide an intraocular lens implanting device wherein the intraocular lens is prevented from rotating improperly when the intraocular lens is inserted into the eye, the intraocular lens can be safely and reliably inserted into the eyeball, and the device has an ophthalmic hooking function whereby the position of the intraocular lens can be adjusted after the intraocular lens has entered the eyeball.

Means for Solving These Problems

The invention according to a first aspect provides an intraocular lens implanting device for inserting an intraocular lens into an eyeball through an incision in the eyeball tissue, the device characterized in including a cylindrical main body, a storage part for the intraocular lens that is integrated with or is separate from the main body, and a plunger for pushing out the intraocular lens stored in the storage part and discharging the lens into the eyeball, wherein a distal end of the plunger has a base part and a protuberance.

The invention according to a second aspect is the intraocular lens implanting device according to the first aspect, characterized in that a distal end of the base part is a flat surface.

The invention according to a third aspect is the intraocular lens implanting device according to the first or second aspect, characterized in that the protuberance is provided at one location on the distal end of the base part.

The invention according to a fourth aspect is the intraocular lens implanting device according to any of the first though third aspects, characterized in that the protuberance is provided at a position displaced from the axial center of the plunger.

The invention according to a fifth aspect is the intraocular lens implanting device according to any of the first through third aspects, characterized in that the protuberance is provided at a position displaced from the longitudinal axial center on the distal end surface of the plunger.

The invention according to a sixth aspect is the intraocular lens implanting device according to any of first through fifth aspect, characterized in that the shape of the protuberance is a cylindrical pillar, a hemisphere, or a combination of a cylindrical pillar and a hemisphere.

The invention according to a seventh aspect is characterized in that a contact part of an intraocular lens is elastically deformed by the (*1) protuberance when the intraocular lens stored in the (*1) storage part is pushed and moved by a distal end of the (*1) plunger.

According to the intraocular lens implanting device of the first aspect, the intraocular lens is not likely to be scratched because the pressure applied to the intraocular lens from the distal end of the plunger is properly distributed when the intraocular lens is passed through the interior of the cartridge as a storage part. The device can also have an ophthalmic hooking function because the protuberance in the distal end of the plunger can move and set the intraocular lens in place at a specific position in the eye even after the intraocular lens has been inserted into the eyeball.

According to the intraocular lens implanting device of the second aspect, the intraocular lens can be pushed out in a straight line.

According to the intraocular lens implanting device of the third aspect, the intraocular lens can be elastically deformed in a reliable manner by a specific amount.

According to the intraocular lens implanting device of the fourth aspect, since the protuberance is offset from the axial center of the plunger, the position of the intraocular lens implanted in the eyeball can easily be adjusted by somewhat rotating the hand piece main body.

According to the intraocular lens implanting device of the fifth aspect, the position of the intraocular lens can be more easily adjusted, and there is less danger of the supporting parts of the intraocular lens being damaged.

According to the intraocular lens implanting device of the sixth aspect, the intraocular lens can be elastically deformed in a reliable manner by a specific amount, and the intraocular lens is not scratched.

According to the intraocular lens implanting device of the seventh aspect, the position of the intraocular lens is easily adjusted when the intraocular lens is inserted and implanted into the eyeball.

DETAILED DESCRIPTION OF THE INVENTION

Figure 1:
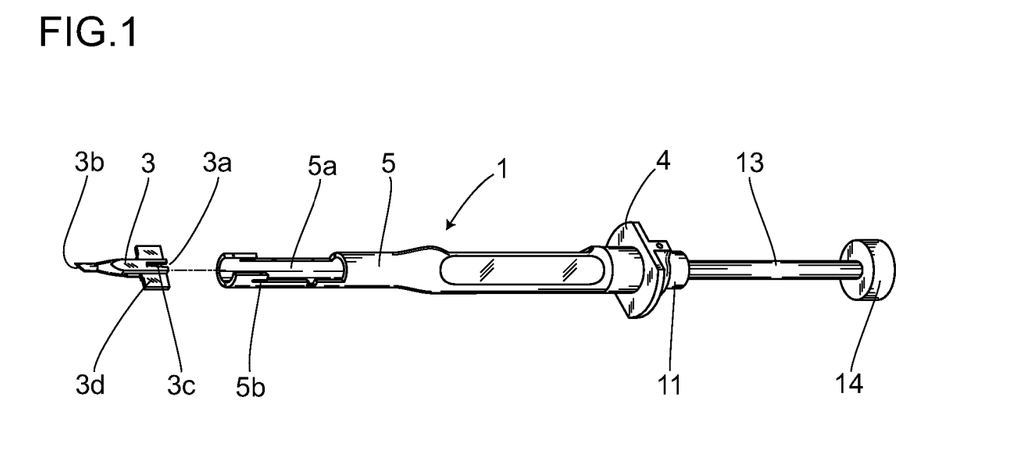
FIG. 1 is an external perspective view of the intraocular lens implanting device according to the present invention.
Figure 2:
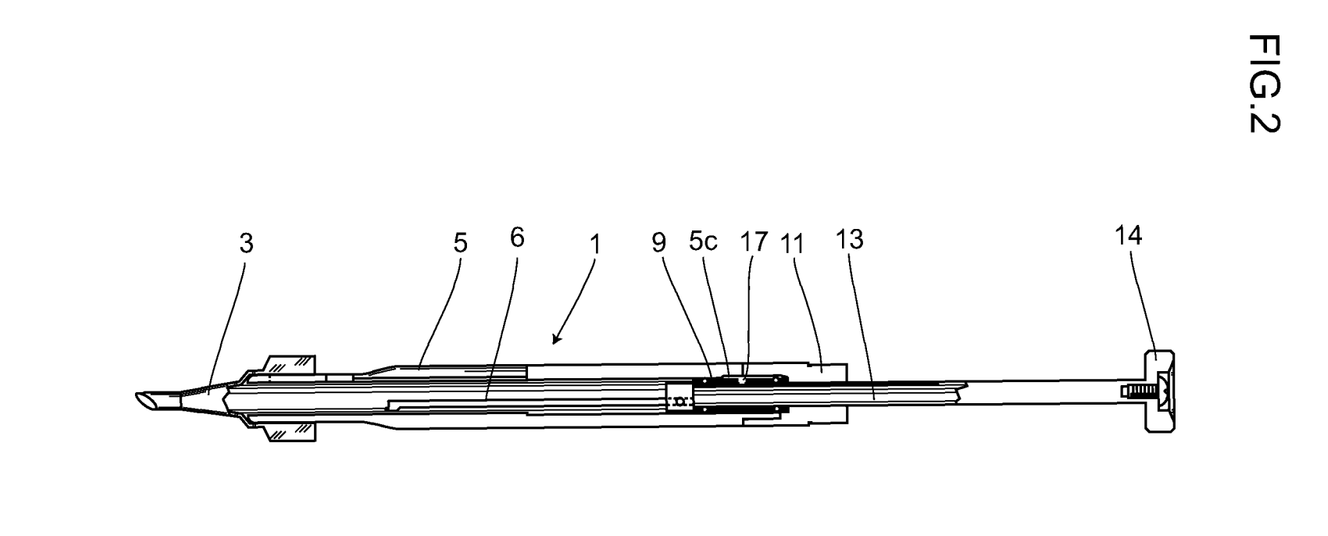
FIG. 2 is a cross-sectional view of the same intraocular lens implanting device.
Figure 3:
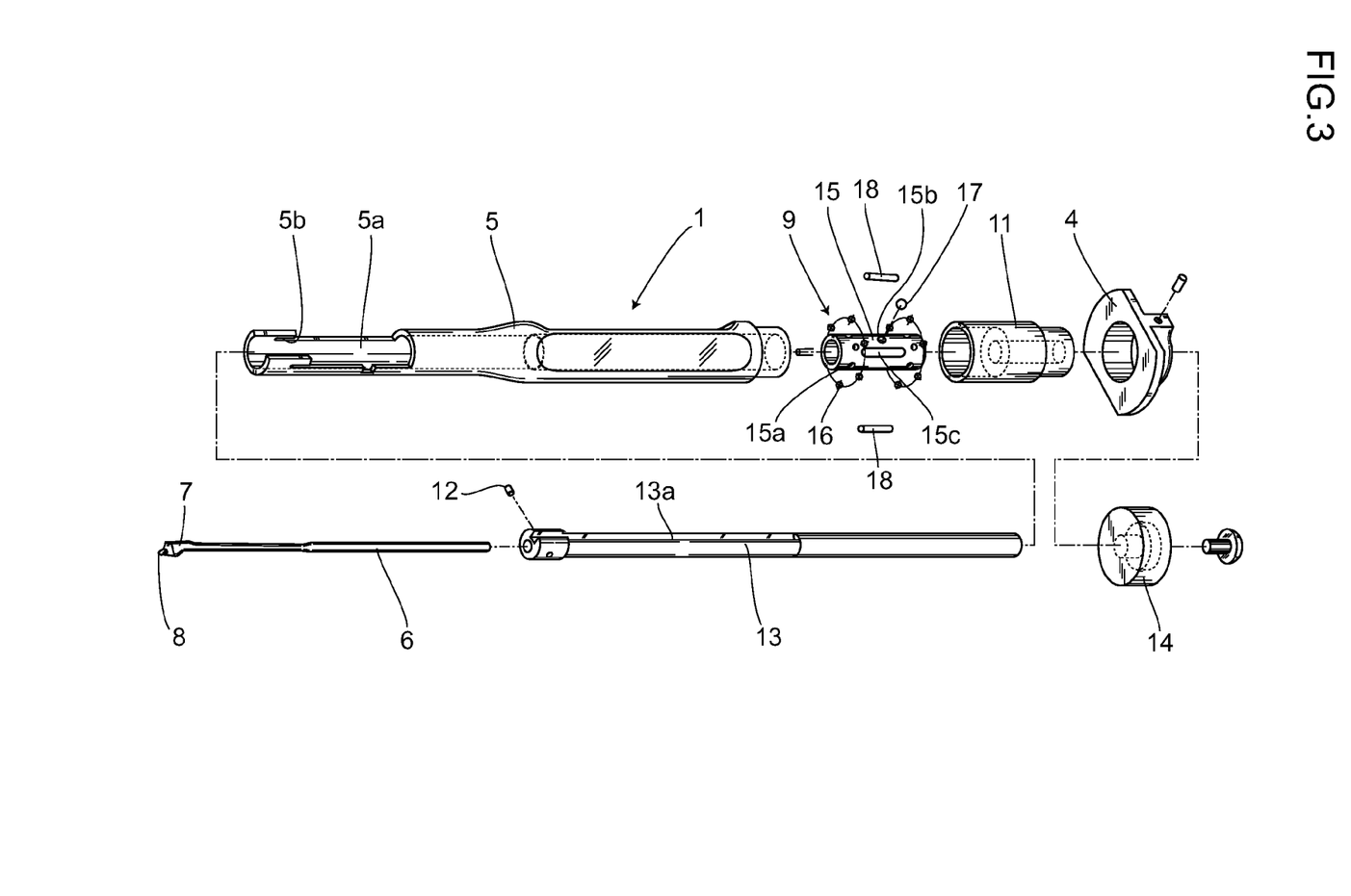
FIG. 3 is a partial exploded view of the same intraocular lens implanting device.

Embodiments of the present invention will now be described with reference to the drawings. FIG. 1 is an external perspective view of an intraocular lens implanting device relating to the present invention, and FIG. 2 is a cross-sectional view of the same. FIG. 3 is a partial exploded view of the intraocular lens implanting device.

First, an intraocular lens implanting device 1 to which the present invention is applied will be described. The general configuration of the intraocular lens implanting device 1 to which the present invention is applied has a cartridge 3 as a storage part for an intraocular lens 2, a cylindrical hand piece 5 as a main body in which the cartridge 3 is fastened at one end and a holding flange 4 is fixed in place at the other end, and a plunger 6 that passes through the hand piece 5 and is integrated with a push rod 13. A distal end 6a of the plunger 6 is configured from a base part 7 and a protuberance 8.

In the cartridge 3, the intraocular lens 2 is stored in the interior, and the distal end is inserted into the eyeball through an incision in the eyeball tissue to discharge the lens into the eyeball. The cartridge has a substantially hollow cylindrical shape, which is tapered at one end. The end of the cartridge 3 on the side nearer to the operator has an intraocular lens insertion hole 3a, and the other end, which is the distal end, has an intraocular lens discharge hole 3b. The insertion hole 3a is used to fold and load the intraocular lens 2 into the cartridge 3, and is provided with an insertion groove 3c in the cylindrical part. This insertion groove 3c allows the intraocular lens 2 to be folded and easily loaded into the cartridge 3 by using an insertion implement (not shown). The incision is formed at a slant to make it easier to insert the discharge hole 3b positioned at the distal end of the cartridge 3 into the incision in the eyeball tissue. Furthermore, two winged parts 3d for fastening the cartridge 3 in the hand piece 5 are provided on the sides of the cartridge 3.

In the present embodiment, the cartridge 3 as the storage part of the intraocular lens and the hand piece 5 as the main body are configured separately, but the cartridge 3 and the hand piece 5 can also be configured integrally.

The hand piece 5 has a guiding part 5a formed in a semi-circular arc in cross section in the side surface nearer to the distal end, and this guiding part has guiding paths for guiding the winged parts 3d of the cartridge 3. Fastening parts 5b that enable the winged parts 3d of the cartridge 3 to be fastened are provided in the distal end side of the guiding part 5a. At the other end of the hand piece 5, a ball bushing 9 is mounted between the external peripheral surface of the push rod 13 and the internal peripheral surface of the hand piece 5. Furthermore, a cap 11 is fixed in place at the other end of the hand piece 5, and a holding flange 4 for allowing the operator to easily hold the hand piece is fixed in place on this cap 11.

The push rod 13 is integrated with the plunger 6 by means of a securing part 12, and is passed through the ball bushing 9 and the holding flange 4 together with the previously described hand piece 5. An end plate 14 for making it easier to push and pull the push rod 13 is fixed in place on the side of the push rod 13 nearer to the operator.

The ball bushing 9 is one type of bearing, provided with multiple holes 15a around the periphery of a cylindrical ball holder 15, wherein metal balls 16 are disposed in these holes 15a and the push rod 13 can be moved with low friction within the cap 11. Specifically, the advantages of this arrangement are that the push rod 13 can be moved within the cap 11 by means of rolling resistance, and only a small amount of drive force is needed to move the push rod 13. The push rod 13 needs only to move in the axial direction, and does not need to rotate in the circumferential direction. In view of this, a groove 13a is provided at one location in the outer peripheral surface of the push rod 13, other holes 15b that are separate from the holes 15a are provided in the ball holder 15 to correspond with the groove 13a, and metal balls 17 that are secured in the holes 15b are caused to engage the groove 13a. The metal balls 17 are also caused to engage an axial groove 5c provided at one location in the internal peripheral surface of the hand piece 5. The push rod 13 is thereby allowed to move in the axial direction within the cap 11, but is prevented from rotating in the circumferential direction.

Furthermore, four long holes 15c are provided in the periphery of the ball holder 15 of the ball bushing 9, and resistance control members 18 are disposed in the long holes 15c. These resistance control members 18 have a slightly larger dimension than the space formed between the minor diameter of the cap 11 and the major diameter of the push rod 13. Specifically, rod-shaped elastic bodies 18 composed of silicon rubber or the like are provided. A suitable amount of slip resistance can thereby be applied to the push rod 13 when the push rod 13 is moved in the axial direction within the cap 11, and the movement resistance and speed of the push rod 13 can be controlled. The reason the push rod 13 is thus provided with a suitable amount of slip resistance is because when the resistance of the push rod 13 is too small, the plunger 6 integrated with the push rod 13 cannot maintain its own position without assistance, which makes it more difficult to insert and implant the intraocular lens 2 into the eyeball.

The intraocular lens implanting device 1 to which the present invention is applied makes it possible to control the movement resistance and speed of the push rod 13 by using the ball bushing 9 provided with the resistance control members 18 as described above, and the intraocular lens 2 can therefore be prevented from being suddenly discharged into the eyeball. Since the resistance control members 18 are embedded in the long holes 15c in the ball holder 15, durability can be improved in comparison with a configuration in which the resistance control members 18 are embedded within the hand piece 5 or the cap 11. Furthermore, durability can be further improved if the rod-shaped resistance control members 18 embedded in the long holes 15c of the ball holder 15 are curved into arc shapes.

The intraocular lens implanting device 1 described above uses a ball bushing 9 as a member for controlling the movement resistance and speed of the push rod 13, but a sliding bearing made of a resin as a low-friction material can also be used instead of the ball bushing 9. Teflon (registered trademark) and PEEK are examples of a resin material having a low coefficient of friction. A sliding bearing manufactured from these resin materials is less expensive than a ball bushing 9 and has the advantage of keeping production costs low.

The intraocular lens implanting device 1 to which the present invention is applied is a medical implement, and the materials of the structural components of this implement must therefore be physically and chemically stable. Particularly, the material used in the region inserted into the eye must be guaranteed to be biologically stable. Possible examples include materials that are approved as implant materials by the FDA (Food and Drug Administration), materials that are standardized as implant materials by the ISO (International Standardization Organization), or materials that are confirmed to be free of problems as a result of tests performed according to ISO10993. Examples of materials that fulfill these requirements include polyethylene or polypropylene for the material of the cartridge, and a titanium alloy or martensite stainless steel for the material of the plunger.

It is assumed that the intraocular lens implanting device 1 to which the present invention is applied is a device that an operator can use with one hand, and the dimensions and weight of the intraocular lens implanting device 1 are also important factors. Specifically, it is difficult to operate the device with one hand if the dimensions are either too large or too small. There is no inconvenience for the device to be lightweight, but a device that is too heavy increases the burden on the operator. According to empirical fact, the maximum length of the entire device with the push rod 13 extended is preferably 200 mm or less, and more preferably 160 mm or less. The weight of the entire intraocular lens implanting device 1 is preferably 40 g or less, and more preferably 30 g or less.

In view of this, in the intraocular lens implanting device 1 to which the present invention is applied, a material having a high specific strength, i.e., a material having a high strength per unit weight is used as the material of the primary components. Specifically, a titanium alloy is primarily used, but stainless steel is also used for the screws and other small components. As a result of using such materials, it is possible to attain an intraocular lens implanting device 1 that is free of rust, is lightweight, and has superior durability as described hereinbelow.

The intraocular lens implanting device 1 to which the present invention is applied requires no maintenance under normally assumed conditions. The device can retain its initial performance after a period of two years or more, without any special maintenance. It has also been confirmed that the device can retain its initial performance even after being repeatedly treated 200 or more times when the treatment is high-pressure sterilization conducted at 130° C. for fifteen minutes. Furthermore, it has been confirmed that the device retains its initial performance when a thrust load of 800 g is applied to the distal end of the plunger 6, even when such a load is repeatedly applied 100 or more times. It has also been confirmed that the device can withstand 10,000 operating cycles in a load-free state in which no load is applied to the plunger 6.

Figure 4A:
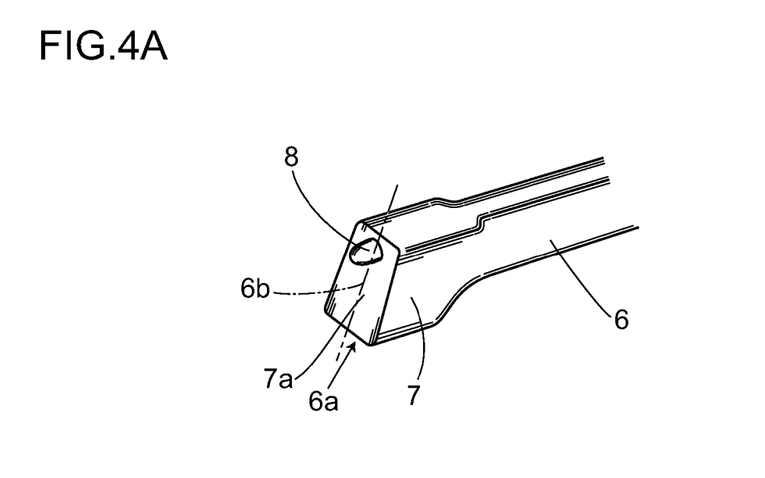
FIG. 4 is a perspective view showing the shape of the distal end of the plunger of the same device.
Figure 4B:
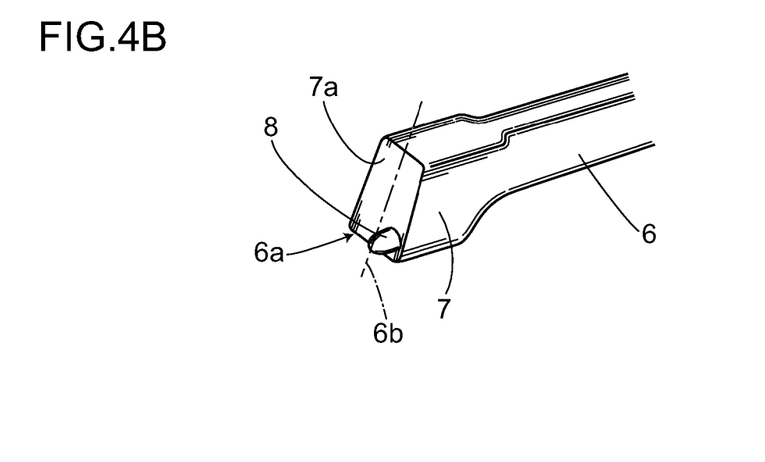
Figure 4C:
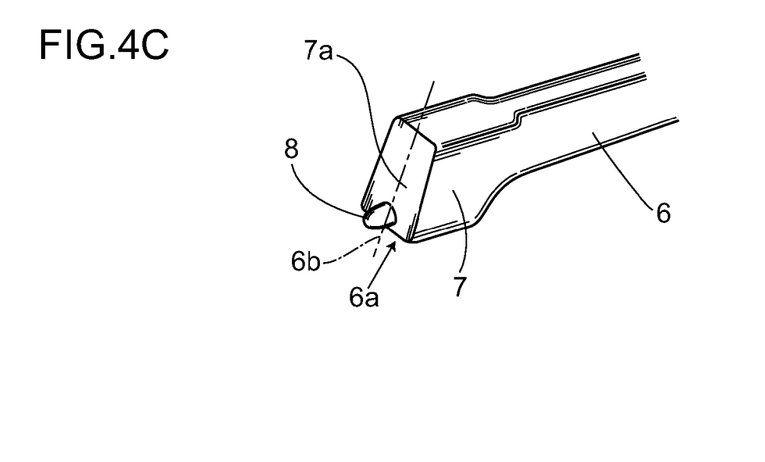

The following is a description, made with reference to FIG. 4, of the shape of the distal end 6a of the plunger 6, which is in the core portion of the present invention. The distal end 6a of the plunger 6 is configured from a base part 7 and a protuberance 8. FIG. 4 shows different examples of the shape of the distal end of the plunger 6, wherein (a) depicts a case in which the protuberance 8 is provided in the top center of the distal end of the base part 7, (b) depicts a case in which the protuberance 8 is provided at the lower right of the distal end of the base part 7, and (c) depicts a case in which the protuberance 8 is provided in the bottom center of the distal end of the base part 7. The common aspect shared by these examples is that the protuberance 8 is provided to one location on the distal end of the base part 7 whose distal end is a flat surface, and the protuberance 8 is provided at a position displaced from the axial center of the plunger 6. The difference is that the positions of the protuberance 8 shown in (a) and (c) are provided in the longitudinal axis center 6b of the distal end surface of the plunger 6, while the position of the protuberance 8 shown in (b) is provided at a position displaced from the longitudinal axis center 6b of the distal end surface of the plunger 6.

In each example shown in FIG. 4, arbitrary values can be used for the dimensions of the distal end 6a of the plunger 6 and the protuberance 8, but appropriate values exist for the distal end 6a of the plunger 6 and the protuberance 8 because the intraocular lens 2 will be inserted into the eye. For example, typical dimensions for the intraocular lens 2 are 6 mm for the diameter of the optical part, 0.7 mm for the center thickness of the optical part, and 0.25 mm for the peripheral thickness of the optical part. In this case, a width of 1.2 mm and a height of about 1.5 mm are suitable dimensions for the distal end 6a of the plunger 6. A diameter and height of about 0.3 mm are suitable dimensions for the protuberance 8.

The plunger 6 is integrated with the push rod 13 and is pushed and pulled by the operator. The intraocular lens 2 stored in the cartridge 3 is pushed out and implanted into the eye by the distal end 6a of the plunger 6. The intraocular lens is made of bendable material and is highly elastic. Therefore, when the periphery 2a of the intraocular lens 2 is pressed in, the periphery 2a of the intraocular lens deforms comparatively easily, but returns to its pre-deformation state when the pressure is released. Each of the distal ends 6a of the plungers 6 shown in FIG. 4 is used to press on the periphery 2a of the intraocular lens, the protuberance 8 comes into contact with the periphery 2a of the intraocular lens, and the periphery 2a of the intraocular lens is first pressed by the protuberance 8. The optimum shape for the protuberance 8 is a hemisphere or a combination of a hemisphere and a cylindrical pillar, and since the protuberance has a small surface area, the periphery 2a of the intraocular lens in contact with the protuberance 8 is subjected to comparatively high surface pressure. The protuberance 8 presses into the periphery 2a of the intraocular lens and causes the contact part of the intraocular lens to undergo elastic deformation. As the protuberance 8 causes the intraocular lens 2 to undergo elastic deformation, the periphery 2a of the intraocular lens comes into contact with a flat surface 7a at the distal end of the base part 7. Therefore, the amount of deformation in the intraocular lens 2 caused by the protuberance 8 is limited by the height of the protuberance 8 from the distal end surface 7a of the bottom part. When the intraocular lens 2 is pressed by the plunger 6, the periphery 2a of the intraocular lens is pressed by the flat surface 7a at the distal end of the base part 7. Therefore, the height of the protuberance 8 is set so as to not exceed the elasticity limit of the material of the intraocular lens 2.

The shape of the protuberance 8 is not limited to a hemisphere or a combination of a hemisphere and a cylindrical pillar, and may be a cylindrical pillar alone or an elliptical pillar.

The reason that the protuberance 8 is provided at a position displaced from the axial center of the plunger 6, i.e., at the periphery of the distal end surface 7a at the base that is offset from the axial center of the plunger 6, is that the protuberance 8 can then easily come into contact with the periphery 2a of the intraocular lens, which is bent into the shape of a U. Because of this, the position to which the protuberance 8 is provided should be the periphery of the distal end surface 7a at the base, and this position is not limited to the examples shown in FIGS. 4(a), (b), and (c).

Figure 5:
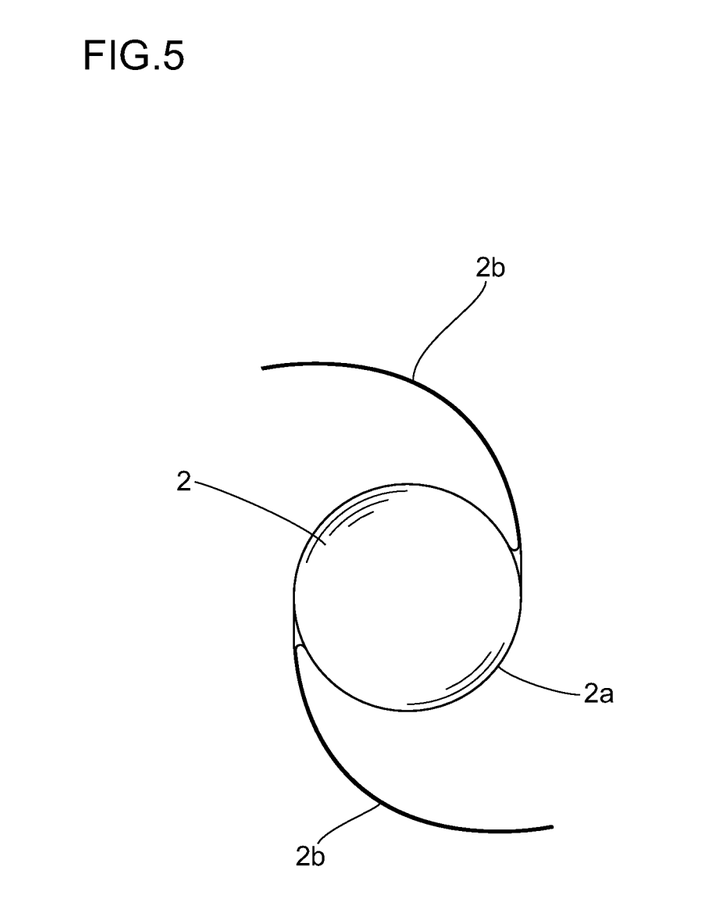
FIG. 5 is a drawing showing a plan view of an intraocular lens.
Figure 6:
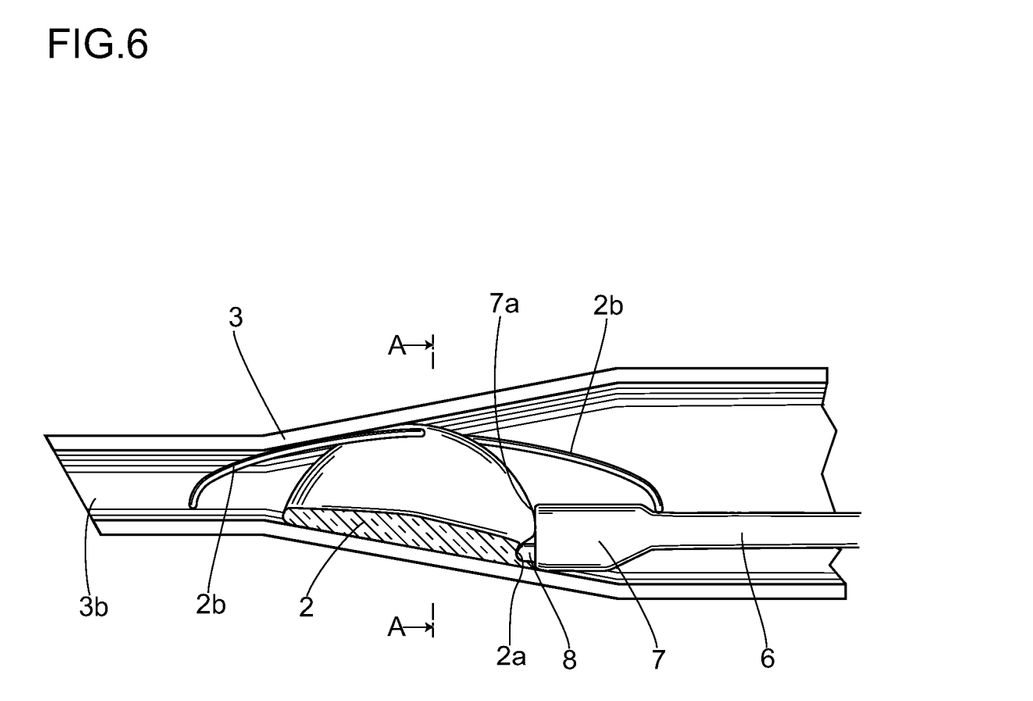
FIG. 6 is a cross-sectional view showing the manner in which the intraocular lens is stored in the cartridge.
Figure 7:
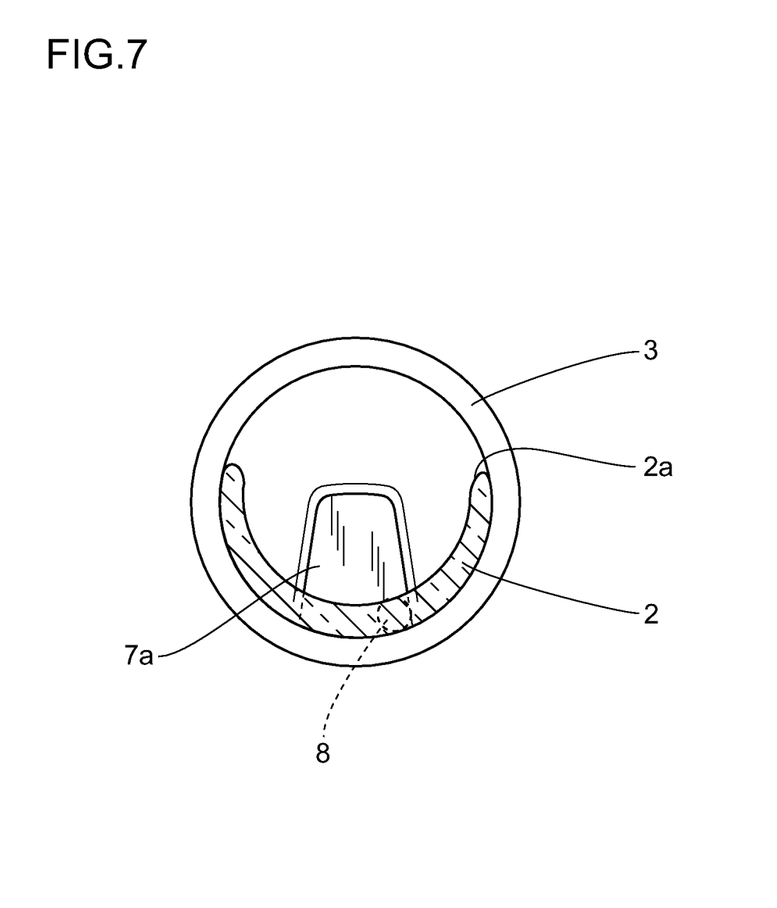
FIG. 7 is a view from the arrows A-A in FIG. 6.
Figure 8A:
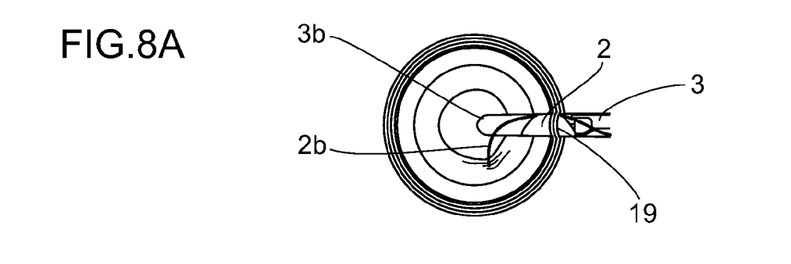
FIG. 8 is a schematic view showing the process of implanting the intraocular lens in an eyeball.
Figure 8B:
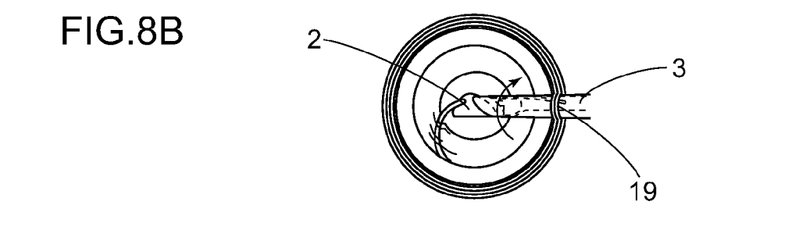
Figure 8C:
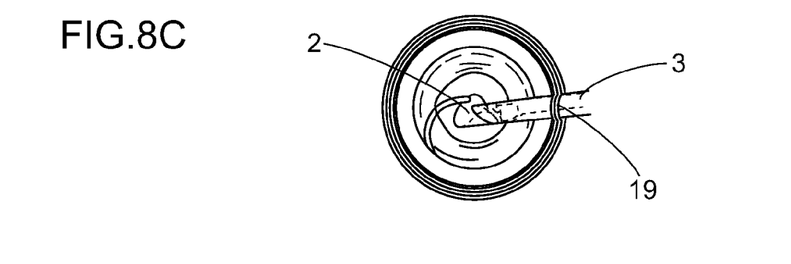
Figure 8D:
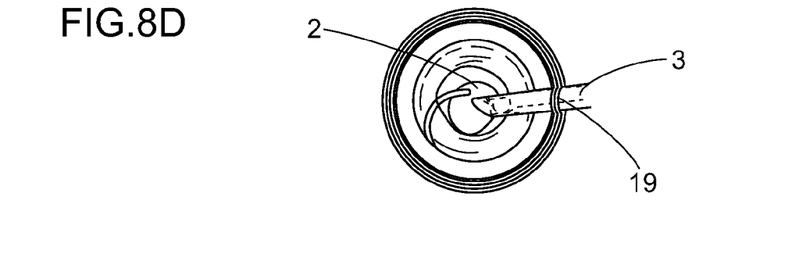
Figure 8E:
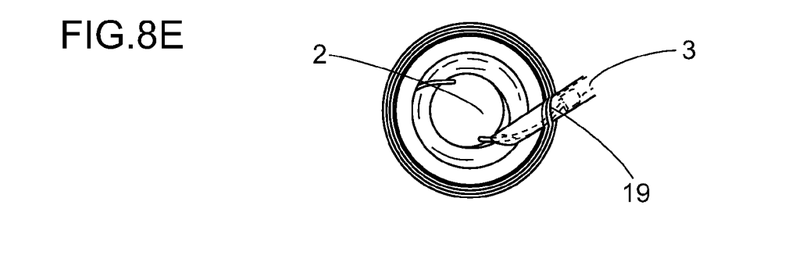

The following is a description, made with reference to FIGS. 5 through 7, of the action when the intraocular lens 2 is inserted and implanted into an eyeball by using the intraocular lens implanting device 1 to which the present invention is applied. FIG. 5 shows a plan view of the intraocular lens 2. The intraocular lens 2 is composed of an optical part 2 as a lens main body having a substantially circular plate shape, and two barb-shaped supporting parts 2b for fixing the position of the optical part 2. The lens is made of a soft resin material, including the optical part 2, and can easily undergo elastic deformation. FIG. 6 shows the manner in which the optical part 2 is folded into a substantial U shape and stored in the cartridge 3, and is pressed and moved by the distal end of the plunger 6. Specifically, this drawing is an axial cross-sectional view of the cartridge 3. FIG. 7 is a view from the arrows A-A in FIG. 6.

The intraocular lens 2 is stored in the cartridge 3 so that the mounts of the two support parts 2b are positioned at the two ends of the U shape. Therefore, after the lens is stored in the cartridge 3, the two support parts 2b are disposed on the front and back of the cartridge 3 in the axial direction, as shown in FIG. 6. The distal end 6a of the plunger 6 comes into contact with the periphery 2a of the optical part of the optical part 2 so as to avoid the barb-shaped support parts 2b.

After the cartridge 3 that stores the intraocular lens 2 is mounted in the intraocular lens implanting device 1, the operator uses one hand to push out the intraocular lens 2 from the distal end of the cartridge 3 and implant the lens in the eyeball. Specifically, the lens is implanted by the procedure shown in the drawings in FIG. 8. First, the protuberance 8 provided at the distal end of the base part 7 of the plunger 6 comes into contact with and presses against the periphery 2a of the optical part, and also presses against the flat surface 7a of the distal end of the base part 7 of the plunger 6 to move the intraocular lens 2 closer to the distal end of the cartridge 3. At this time, the intraocular lens 2 generates sliding resistance by being caused to slide against the internal peripheral surface of the cartridge 3. The intraocular lens 2 moves toward the distal end within the cartridge 3 when the plunger 6 applies pressure greater than this sliding resistance.

Since the intraocular lens 2 is made from a soft elastic material, the protuberance 8 at the distal end of the plunger 6 causes the periphery 2a of the optical part to undergo significant elastic deformation, and the flat surface 7a of the base part 7 of the plunger 6 also elastically deforms the periphery 2a of the optical part with a certain amount of pressure. As a result, the distal end 6a of the plunger 6 is essentially fixed in place on the periphery 2a of the intraocular lens, and the protuberance 8 at the distal end of the plunger 6 exhibits the effect of an anchor. Therefore, the operator can easily move the intraocular lens 2 within the cartridge 3 while keeping the intraocular lens 2 in the intended alignment.

The following is a simple description, made with reference to FIG. 8, of the process for inserting and implanting the intraocular lens 2 into the eyeball. The discharge hole 3b of the cartridge 3 is inserted into the incision 19 in the eyeball, and the distal end support part 2b is inserted into the eye, as shown in (a). The plunger 6 then pushes out the intraocular lens 2 in small increments while the entire intraocular lens implanting device 1 is slowly rotated to open the optical part 2, as shown in (b) and (c). The intraocular lens 2 is not necessarily moved to the optimal position in the eyeball in this stage. In many cases, the position of the intraocular lens 2 in the eyeball must be adjusted. The drawing in (d) shows an example of this, wherein the position of the intraocular lens 2 is adjusted with the aid of the plunger 6 by using the fact that the protuberance 8 provided at the distal end of the plunger 6 is still pushed into the periphery 2a of the optical part. The other supporting part 2b is released from the cartridge 3 as shown in (e) after the position of the intraocular lens 2 has been adjusted.

When the intraocular lens 2 is moved within the cartridge 3 in this manner, it is possible to easily control the alignment of the intraocular lens 2 by using the anchor effect in which the protuberance 8 at the distal end of the plunger 6 presses against the periphery 2a of the optical part. Furthermore, the intraocular lens 2 is easily aligned to the desired position inside the eyeball, because the anchor effect remains for some time even after the intraocular lens 2 is discharged from the discharge hole 3b of the cartridge 3 inserted into the eyeball through the incision 19 and has returned to its original plate shape inside the eyeball.

Figure 9A:
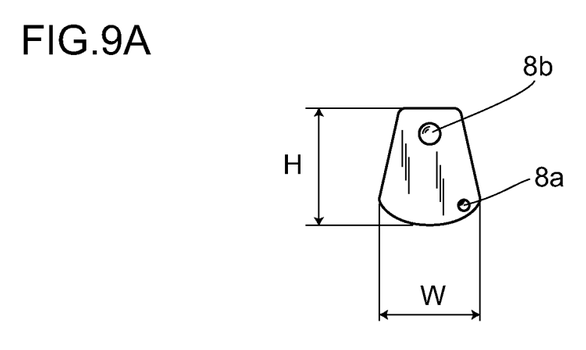
FIG. 9 is a drawing showing the shape of the distal end of the plunger in another example.
Figure 9B:
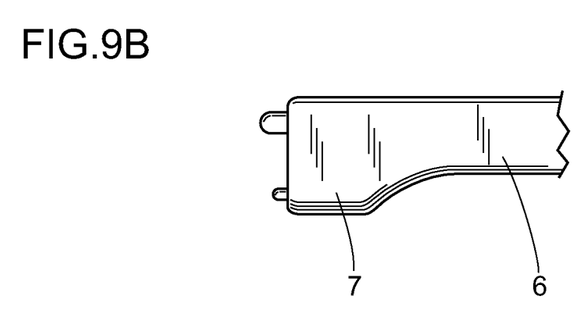

Next, an example will be described in which two protuberances are provided at the distal end of the plunger 6, unlike in FIG. 4. FIG. 9 shows a plunger 6 in which two protuberances are provided at the distal end, wherein (a) is a front view and (b) is a side view. A protuberance 8a provided at the bottom right of the front view exhibits the same anchor effect as the protuberance shown in FIG. 4. This protuberance comes in contact with the periphery of the intraocular lens 2 to elastically deform the intraocular lens 2, and introduces the intraocular lens 2 into the eyeball from the cartridge 3. Assuming that the width W of the distal end 6a of the plunger 6 is 1.2 mm and the height H is 1.5 mm, a diameter of 0.2 mm and a height of about 0.25 mm are suitable dimensions for the protuberance 8a. The protuberance 8b in the top center of the front view is designed to come into contact with the surface of the intraocular lens 2 inside the eyeball and adjust the position of the intraocular lens 2 after the intraocular lens 2 is discharged into the eyeball from the cartridge 3. Providing this protuberance 8b makes it possible to easily adjust the position of the intraocular lens 2 inside the eyeball. A diameter of 0.26 mm and a height of about 0.43 mm are suitable dimensions for the protuberance 8b.

Several examples of the present invention were described above, but the present invention is not limited to these examples, and various modifications can be made. For example, in the examples described above, the present invention was applied to an intraocular lens implanting device 1 in which the plunger 6 was moved by pushing and pulling directly in the axial direction, but it is apparent that the present invention can also be applied to a screw-style intraocular lens implanting device wherein the plunger 6 is moved by the rotation of the push rod.

In FIGS. 6 through 8, an example was described in which the intraocular lens was folded into a substantial U shape, but the cross-sectional shape of the intraocular lens when folded is not limited to the shape of a U, and the lens can be folded into various other cross-sectional shapes.

The invention claimed is:

1. An intraocular lens implanting device for inserting an intraocular lens into an eyeball through an incision in the eyeball tissue, said intraocular lens implanting device comprising:
   a cylindrical main body;
   a storage part for the intraocular lens that is integrated with or is separate from the main body; and
   a plunger, for pushing out the intraocular lens stored in the storage part and discharging the lens into the eyeball, that has a distal end including
      a base part having a flat surface with an outer boundary defined by an edge, a height, a width, a first axis defined by a center of the height, and a second axis defined by a center of the width, and
      a protuberance, including a base end, with a center, that is adjacent to the flat surface and a free end that is distal of the base end, disposed on a periphery of the flat surface at a distance from the outer boundary of the flat surface, such that the base end of the protuberance is disposed entirely within an area defined by the outer boundary of the flat surface and the center of the base end is offset from the first and second axes, and
   wherein both the flat surface and the protuberance contact an optical part of the intraocular lens.

2. The intraocular lens implanting device according to claim 1, wherein the shape of the protuberance is a cylindrical pillar, a hemisphere, or a combination of a cylindrical pillar and a hemisphere.

3. The intraocular lens implanting device according to claim 1, wherein a contact part of an intraocular lens is elastically deformed by the protuberance when the intraocular lens stored in the storage part is pushed and moved by a distal end of the plunger.

4. The intraocular lens implanting device according to claim 1, wherein the flat surface and the protuberance fixes the distal end of the plunger to the intraocular lens.

5. An intraocular lens implantation device for use with an intraocular lens having an optical part, the implantation device comprising:
   a tubular main body;
   an intraocular lens storage portion associated with the main body; and
   a plunger, movable through the intraocular lens storage portion, including
      a distal end flat surface that has an outer boundary defined by an edge, and
      a substantially rigid protuberance that extends distally from the flat surface and is offset from the outer boundary of the flat surface;
   wherein the plunger and intraocular lens storage portion are configured such that both the flat surface and the protuberance contact an optical part of the intraocular lens.

6. An intraocular lens implantation device as claimed in claim 5, wherein the tubular main body comprises a cylindrical main body.

7. An intraocular lens implantation device as claimed in claim 5, wherein the intraocular lens storage portion comprises a removable cartridge.

8. An intraocular lens implantation device as claimed in claim 5, wherein the intraocular lens storage portion is integral with the tubular main body.

9. An intraocular lens implantation device as claimed in claim 5, wherein the plunger is formed from a metal.

10. An intraocular lens implantation device as claimed in claim 9, wherein the metal comprises a titanium alloy or stainless steel.

11. An intraocular lens implantation device as claimed in claim 5, wherein the protuberance is a cylindrical pillar, a hemisphere, or a combination of a cylindrical pillar and a hemisphere.

12. An intraocular lens implantation device as claimed in claim 5, wherein the flat surface and the protuberance together fix the distal end of the plunger to the intraocular lens.

13. An intraocular lens implantation device as claimed in claim 5, wherein the flat surface defines a height, a width, a horizontal axis that passes through the mid-point of the height, and a vertical axis that passes through the mid-point of the width; and the protuberance has a center that is offset from the vertical and horizontal axes.

* * * * *